(12) United States Patent
Nir et al.

(10) Patent No.: US 10,918,473 B2
(45) Date of Patent: Feb. 16, 2021

(54) TRANSCATHETER HEART VALVE STORAGE CONTAINER AND CRIMPING MECHANISM

(71) Applicant: Edwards Lifesciences Corporation, Irvine, CA (US)

(72) Inventors: Noam Nir, Gesher Haziv (IL); Carmel Peleg, Tel Aviv (IL); Tomer Saar, Pardes Hanna-Karkur (IL); Alexander Barash, Tzoran (IL); David Maimon, Haifa (IL)

(73) Assignee: Edwards Lifesciences Corporation, Irvine, CA (US)

( * ) Notice: Subject to any disclaimer, the term of this patent is extended or adjusted under 35 U.S.C. 154(b) by 84 days.

(21) Appl. No.: 16/036,190

(22) Filed: Jul. 16, 2018

(65) Prior Publication Data
US 2019/0021834 A1    Jan. 24, 2019

Related U.S. Application Data

(60) Provisional application No. 62/534,033, filed on Jul. 18, 2017.

(51) Int. Cl.
*A61F 2/24*    (2006.01)
*A61F 2/00*    (2006.01)
*B21D 39/04*   (2006.01)
*A61F 2/95*    (2013.01)

(52) U.S. Cl.
CPC ............ *A61F 2/0095* (2013.01); *A61F 2/24* (2013.01); *A61F 2/9522* (2020.05); *B21D 39/048* (2013.01)

(58) Field of Classification Search
CPC ................................................ A61F 2/0095
See application file for complete search history.

(56) References Cited

U.S. PATENT DOCUMENTS

| 3,409,013 A | 11/1968 | Berry |
| 3,548,417 A | 12/1970 | Kisher |
| 3,587,115 A | 6/1971 | Shiley |
| 3,657,744 A | 4/1972 | Ersek |

(Continued)

FOREIGN PATENT DOCUMENTS

| DE | 2246526 A1 | 3/1973 |
| DE | 0144167 C  | 6/1985 |

(Continued)

OTHER PUBLICATIONS

8483WO01—International Search Report for International Application No. PCT/US2018/042596, completed Nov. 5, 2018.

(Continued)

*Primary Examiner* — Mollie Impink
(74) *Attorney, Agent, or Firm* — Meunier Carlin Curfman LLC; Joel B. German

(57) ABSTRACT

Disclosed herein is a storage container for an expandable prosthetic heart valve that crimps the valve upon opening the container and removal of the valve from the container. The container includes a housing sized to receive the heart valve in its expanded configuration and a crimping mechanism. The crimping mechanism is incorporated into the container and engages the heart valve so as to operably convert the heart valve from its expanded configuration to its smaller crimped configuration upon opening the container and removing the valve.

22 Claims, 15 Drawing Sheets

(56) References Cited

U.S. PATENT DOCUMENTS

| | | |
|---|---|---|
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,068,635 A * | 5/2000 | Gianotti .................... A61F 2/95 |
| | | 29/235 |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |

(56) References Cited

U.S. PATENT DOCUMENTS

| | | |
|---|---|---|
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 9,078,781 B2 | 7/2015 | Ryan et al. |
| 10,245,136 B2 * | 4/2019 | Ino .................. A61F 2/0095 |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0045928 A1 | 3/2003 | Yang et al. |
| 2003/0050694 A1 | 3/2003 | Yang et al. |
| 2003/0100939 A1 | 5/2003 | Yodfat et al. |
| 2003/0135970 A1 | 7/2003 | Thornton |
| 2003/0158597 A1 | 8/2003 | Quiaction et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0054976 A1 | 2/2009 | Tuval et al. |
| 2009/0118826 A1 | 5/2009 | Khaghani |
| 2009/0125118 A1 | 5/2009 | Gong |
| 2009/0143852 A1 * | 6/2009 | Chambers .............. A61F 2/0095 623/1.11 |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2010/0252470 A1 | 10/2010 | Ryan et al. |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0178590 A1 | 7/2011 | Zucker |
| 2011/0218619 A1 | 9/2011 | Benichou et al. |
| 2011/0301703 A1 | 12/2011 | Glazier |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0152659 A1 * | 6/2013 | Maimon ................ B21D 41/04 72/370.25 |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0128819 A1 | 5/2016 | Giordano et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |

(56) References Cited

FOREIGN PATENT DOCUMENTS

| | | |
|---|---|---|
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

* cited by examiner

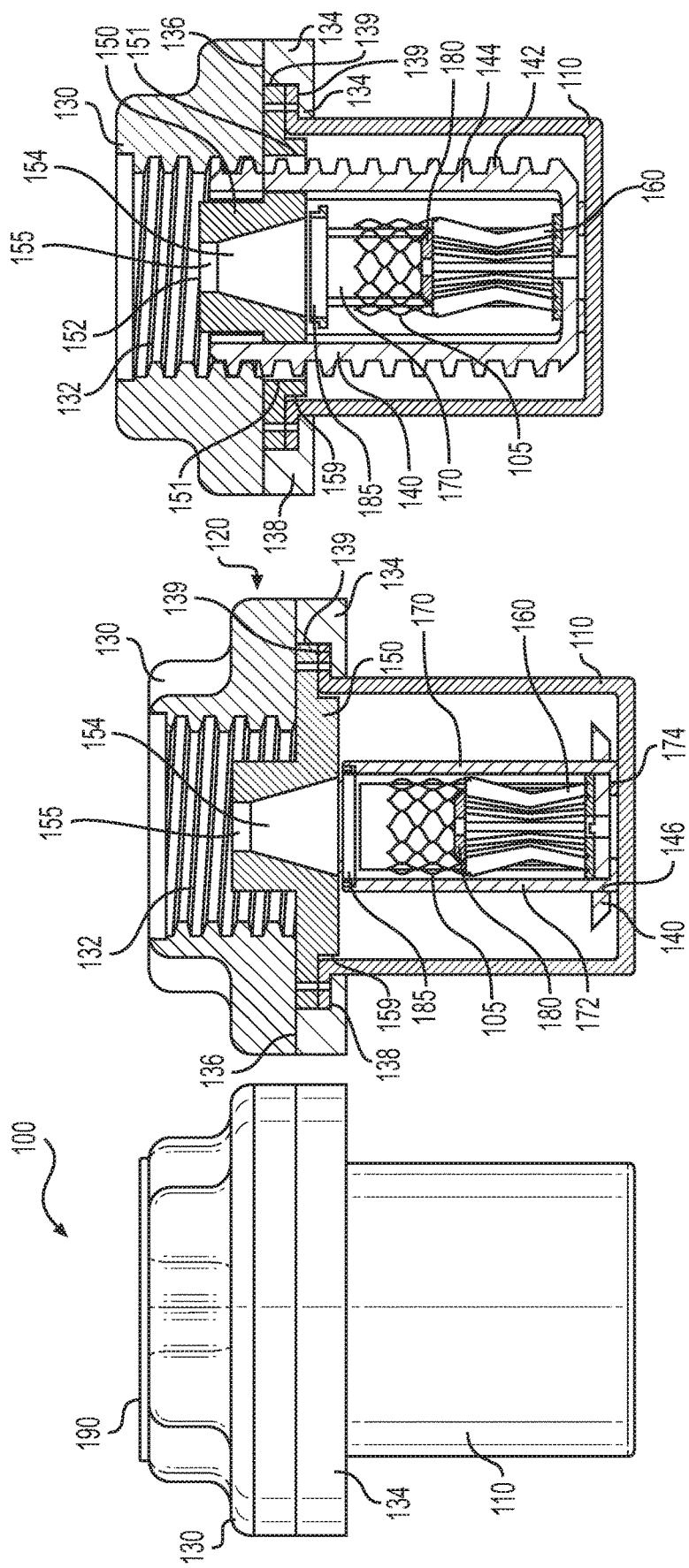

TRANSCATHETER HEART VALVE STORAGE CONTAINER AND CRIMPING MECHANISM

CROSS REFERENCE TO RELATED APPLICATIONS

This application claims the benefit of U.S. Provisional Application No. 62/534,033, filed Jul. 18, 2017, which is incorporated by reference in its entirety for all purposes.

TECHNICAL FIELD

The present invention relates generally to medical devices and particularly to containers and methods for storing and preparing expandable heart valve prostheses for implantation.

BACKGROUND

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves.

Where replacement of a heart valve is indicated, the dysfunctional valve is typically surgically removed and replaced with either a mechanical valve or a tissue valve. Tissue valves are often preferred over mechanical valves because they typically do not require long-term treatment with anticoagulants. The most common tissue valves are constructed with whole porcine (pig) valves, or with separate leaflets obtained from bovine (cow) pericardium. Although so-called stentless valves, comprising a section of porcine aorta along with the valve, are available, the most widely used valves include some form of stent or synthetic leaflet support. Typically, a wireform having alternating arcuate cusps and upstanding commissures supports the leaflets within the valve, in combination with an annular stent and a sewing ring. The alternating cusps and commissures mimic the natural contour of leaflet attachment.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Recently, a great amount of research has been performed to reduce the trauma and risk associated with conventional open heart valve replacement surgery. In particular, the field of minimally invasive surgery (MIS) has exploded since the early to mid-1990s, with devices now being available to enable valve replacements without opening the chest cavity. MIS heart valve replacement surgery still typically requires bypass, but the excision of the native valve and implantation of the prosthetic valve are accomplished via elongated tubes (catheters or cannulas), with the help of endoscopes and other such visualization techniques.

More recently, a variety of prosthetic heart valves have been developed wherein the valve structure is mounted on a stent and then delivered to the implantation site via a percutaneous catheterization technique. Such transcatheter heart valves (THV) are typically crimped to a smaller diameter or profile just prior to implantation.

To minimize the possibility of damage to the relatively delicate tissue type or bioprosthetic heart valves, they are packaged in jars filled with a steriliant and preservative solution for shipping and storage prior to use. In doing so, the valves are stabilized to prevent the valves from contacting the inside of the jar. Prior to implantation in a patient, residual traces of the steriliant and preservative solution are washed from the valve. Washing is accomplished by first removing the valve from the jar and then rinsing the valve in a sterile saline solution. After rinsing, the valve is crimped to reduce it to a size appropriate for transcatheter delivery and implantation. This process leaves the valve susceptible to damage if the valve contacts any surfaces while being manipulated prior to implantation.

There remains a need for a storage and preparation system for such valves that prevents damage to the valve, and enables a medical practitioner to easily and safely remove the valve from the storage container, prepare, and crimp the valve prior to implantation

SUMMARY

Disclosed herein is a storage container for a transcatheter heart valve that allows for the storage of the heart valve in its expanded configuration and permits easy crimping of the heart valve from a larger diameter to a smaller diameter upon removal of the valve from the storage jar prior to implantation. The storage container includes a container housing and a crimping mechanism. The container housing is sized to receive the heart valve in its expanded configuration. The crimping mechanism is incorporated into the container and engages the heart valve to convert the heart valve from its expanded configuration to its crimped or unexpanded configuration upon opening of the container and removal of the valve.

While the present invention is particularly well-suited for use with stented prosthetic heart valves, it can also be applied to other types of stents such as coronary stents, peripheral stents, other stented heart valves and stent grafts.

In some embodiments, the crimping mechanism includes a valve cover coupled to the container housing. The valve cover including a central opening in communication with an interior of the container housing where movement of the heart valve through the central opening converts the heart valve from its expanded configuration to its crimped configuration. The heart valve has a larger diameter in its expanded configuration than in its crimped configuration.

The valve cover can include a tapered channel extending from a bottom surface to the central opening, where movement of the heart valve through the tapered channel upon opening of the container converts the heart valve from its expanded configuration to its crimped configuration. In some embodiments, the tapered channel can define a cone-shaped passage. The size of the opening to the tapered channel at the bottom surface of the valve cover can be designed to correspond to the size of the heart valve in its expanded configuration, while the other end of the channel corresponds to the size of the valve in its crimped configuration.

In some embodiments, the crimping mechanism further includes a top cover coupled to the container housing having an opening axially aligned with the central opening of the valve cover. The crimping mechanism further includes a base structure having a central cavity sized and configured to receive the heart valve. The base is axially movable with respect to the valve cover for moving the heart valve through the central opening of the valve cover. The valve cover can be fixed to the container housing. And the top cover can be rotatably coupled to the container housing and the valve cover. The base includes an exterior thread for engaging a threaded opening in the top cover such that rotation of the top cover causes the threaded opening to engage the exterior threads of the base and move the base axially with respect to the top cover.

In some embodiments, the crimping mechanism further includes a valve stage located within a central cavity of the base, the valve stage providing axial support for the heart valve. In other embodiments, the crimping mechanism includes a valve support extending axially adjacent the heart valve and providing radial or lateral support for the heart valve.

Also disclosed herein is a system for storing and crimping an expandable prosthetic heart valve. The system includes an expandable prosthetic heart valve having both crimped and expanded configurations, the heart valve comprising an annular frame with a leaflet structure positioned within frame. The system also includes a container housing sized to receive the heart valve in its expanded configuration, and a crimping mechanism incorporated into the container housing and engaging the heart valve that is operable to convert the heart valve from its expanded configuration to its crimped configuration upon opening of the container and removal of the heart valve. The heart valve can be a tissue-type valve and the container housing can hold a solution suitable for preserving the leaflet structure.

In some embodiments, crimping mechanism includes a valve cover coupled to the container housing and including a central opening in communication with an interior of the container housing, and a base having a central cavity sized and configured to receive the heart valve. The base is axially movable with respect to the valve cover for moving the heart valve through the central opening of the valve cover. The heart valve is positioned within a central cavity of the base, and movement of the heart valve through the central opening converts the heart valve from its expanded configuration to its crimped configuration.

In some embodiments, the crimping mechanism includes a top cover rotatably coupled to the valve cover and the container housing, the top cover having an opening axially aligned with the central opening of the valve cover. The base includes an exterior thread for engaging a threaded opening in the top cover. The base is rotatably coupled to the top cover and rotation of the top cover causes the threaded opening to engage the exterior threads of the base thereby moving the base axially with respect to the top cover.

In some embodiments, the valve cover includes a tapered channel extending from a bottom surface of the valve cover to the central opening of the valve cover. The size of the opening to the tapered channel at the bottom surface corresponds to the size of the heart valve in its expanded configuration while the other end of the channel corresponds to the size of the valve in its crimped configuration. Movement of the heart valve through the tapered channel converts the heart valve from its expanded configuration to its crimped configuration.

Further disclosed herein is a method of storing and crimping an expandable prosthetic heart valve. The method includes providing a prosthetic heart valve having a crimped configuration sized to be delivered to a site of implantation through a catheter and an expanded configuration sized to engage a heart valve annulus. The method also includes storing the heart valve in a container in its expanded configuration and converting the heart valve from its expanded configuration to its crimped configuration as it passes through an opening in the container. The step of converting further comprises compressing the heart valve through a tapered channel provided in the container.

In some embodiments, the container includes a container housing, a valve cover coupled to the container housing and including a central opening in communication with an interior of the container housing, and a base having a central cavity receiving the heart valve. The base is rotatably coupled to the valve cover and axially movable with respect to the valve cover and container housing. The step of converting the heart valve from its expanded configuration to its crimped configuration further comprises axially moving the base with respect to the valve cover and advancing the heart valve from the central cavity of the base and through the central opening of the valve cover.

In some embodiments, a top cover is rotatably coupled to the valve cover and the container housing. The base can include an exterior thread for engaging a threaded opening in the top cover, where the threaded opening in the top cover is axially aligned with the central opening of the valve cover. The step of converting the heart valve from its expanded configuration to its crimped configuration further comprises rotating the top cover to cause the threaded opening to engage the exterior threads of the base and thereby moving the base axially with respect to the top cover.

In some embodiments, the step of converting the heart valve from its expanded configuration to its crimped configuration further comprises crimping the heart valve and maintaining the heart valve in its crimped state using a constraint around the heart valve. And the method further includes detaching the heart valve from the storage container after placing the constraint around the valve and mounting the valve on a delivery catheter.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 8 is a front view of the storage container of FIG. 5;

FIG. 9A is a section view of the storage container of FIG. 1;

FIG. 9B is a section view of the storage container of FIG. 1;

Like reference symbols in the various drawings indicate like elements.

DETAILED DESCRIPTION

Figure 1:
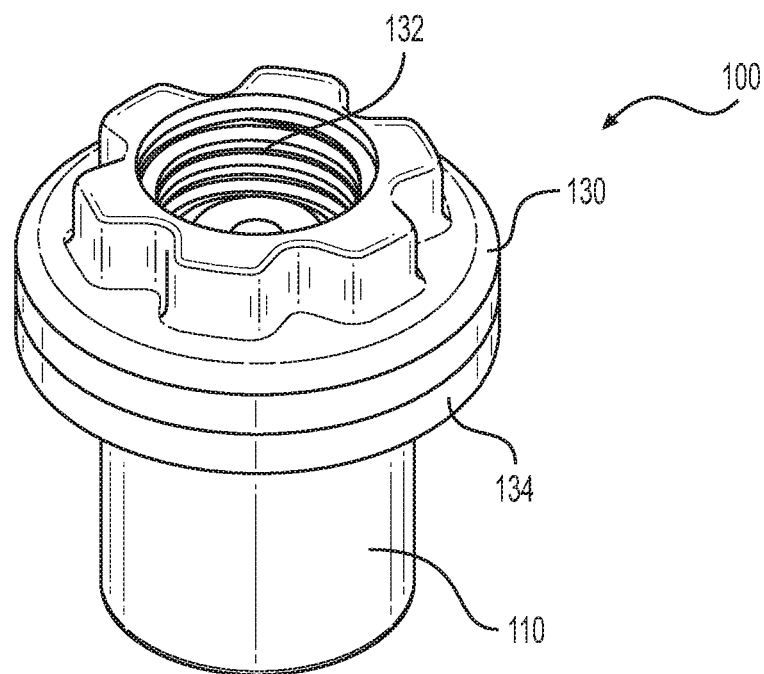
FIG. 1 is a perspective view of an example storage container for a transcatheter heart valve.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of a sheath, catheter, or delivery assembly. "Proximal" means that region closest to handle of the device, while "distal" means that region farthest away from the handle of the device.

The term "tube" or "tubular" as used herein is not meant to limit shapes to circular cross-sections. Instead, tube or tubular can refer to any elongate structure with a closed-cross section and lumen extending axially therethrough. A tube may also have some selectively located slits or openings therein—although it still will provide enough of a closed structure to contain other components within its lumen(s).

Embodiments disclosed herein provide a storage container for a transcatheter heart valve that also facilitates preparation for delivery and implantation of the valve. Transcatheter heart valves come in a variety of designs, including directly radially expandable types (such as balloon expandable valves), self-expanding valves, mechanically expandable valves, and so-called "rolled" heart valves that are spirally wound into a compact configuration that can be expanded by unwinding. While a balloon expandable heart valve is represented herein, it should be understood that the principles disclosed herein are applicable to all types of expandable heart valves, stents and similar medical devices.

The present disclosure is directed to a container for storing, preparing, and handling an expandable prosthetic heart valve prior to implantation. Many transcatheter heart valves include flexible leaflets typically made from animal tissue or other biocompatible natural or synthetic material. The embodiment illustrated represents an expandable prosthetic heart valve having bovine pericardial leaflets. This heart valve is similar to that shown and described in U.S. Pat. No. 9,393,110, entitled "Prosthetic Heart Valve" and expressly incorporated herein by reference. Regardless of the material of the flexible leaflets, it is advantageous to store them in a relaxed state to minimize folding or compression of the leaflets. However, to deliver such expandable heart valves, the overall profile of the valve is made smaller (i.e., crimped) in order to pass through a relatively small diameter delivery catheter, thus requiring folding or compressing of the leaflets.

The container of the present disclosure enables the storage of a heart valve in its expanded configuration to better protect the flexible leaflets during potentially long storage times, and permits easy crimping of the heart valve upon removal from the storage jar prior to implantation.

Figure 2:
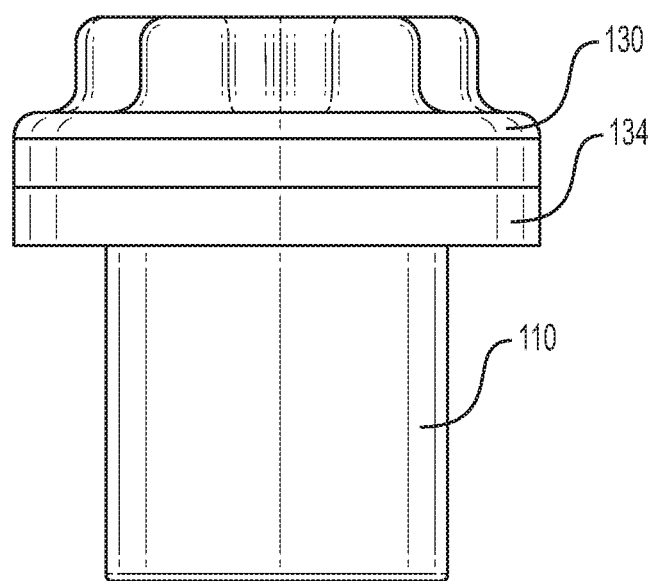
FIG. 2 is a front view of the storage container of FIG. 1.
Figure 3:
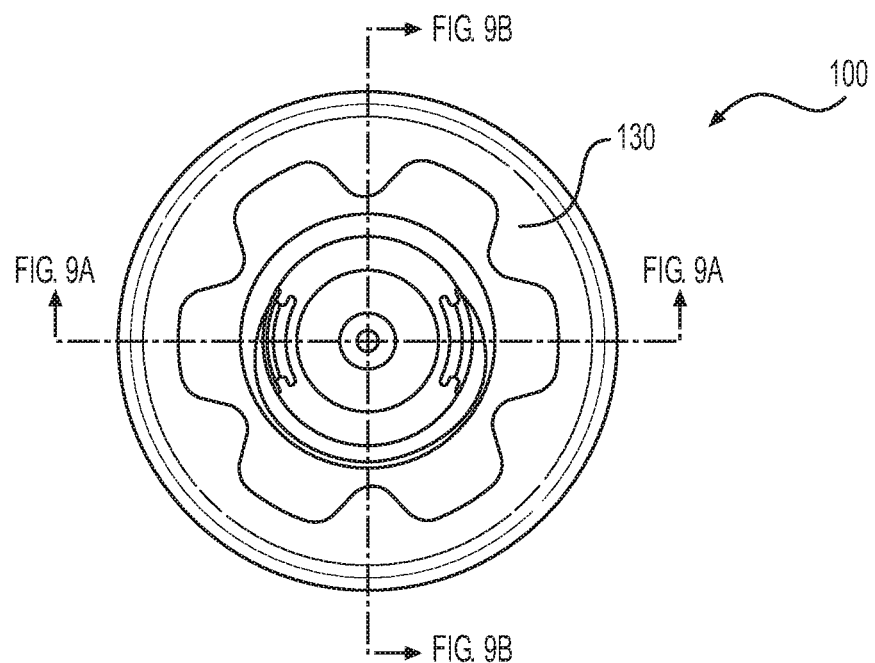
FIG. 3 is a top view of the storage container of FIG. 1.
Figure 4:
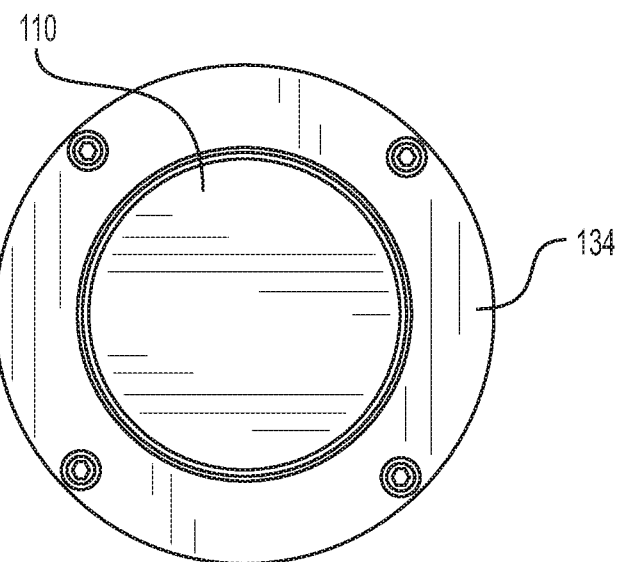
FIG. 4 is a bottom view of the storage container of FIG. 1.

FIG. 1 illustrates an assembled view of an example storage container 100 for a prosthetic heart valve 105, the valve having both expanded and unexpanded configurations. FIG. 2 provides a front elevation of the storage container 100, and FIGS. 3 and 4 provide top and bottom views, respectively. As shown, the storage container 100 includes a container housing 110 sized to receive the heart valve 105 in its expanded configuration (as shown in FIGS. 9A and 9B) and a top cover 130.

Figure 5:
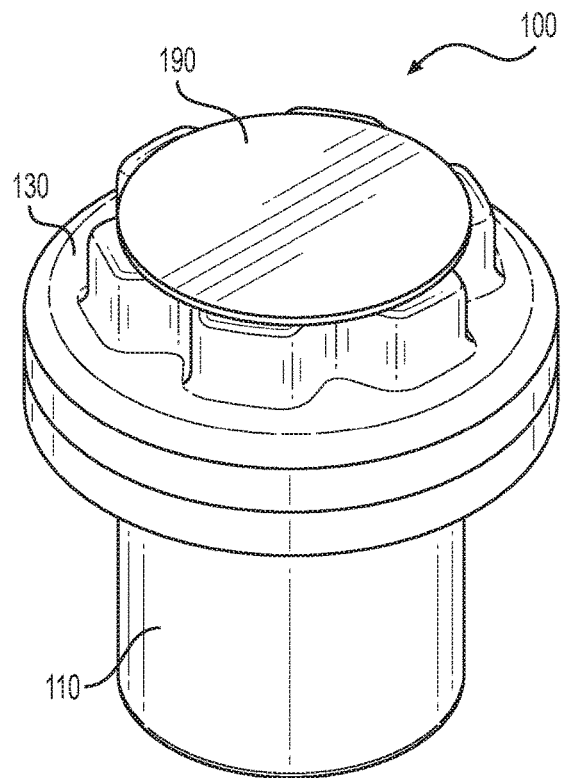
FIG. 5 is a perspective view of the storage container of FIG. 1 including a lid.
Figure 6:
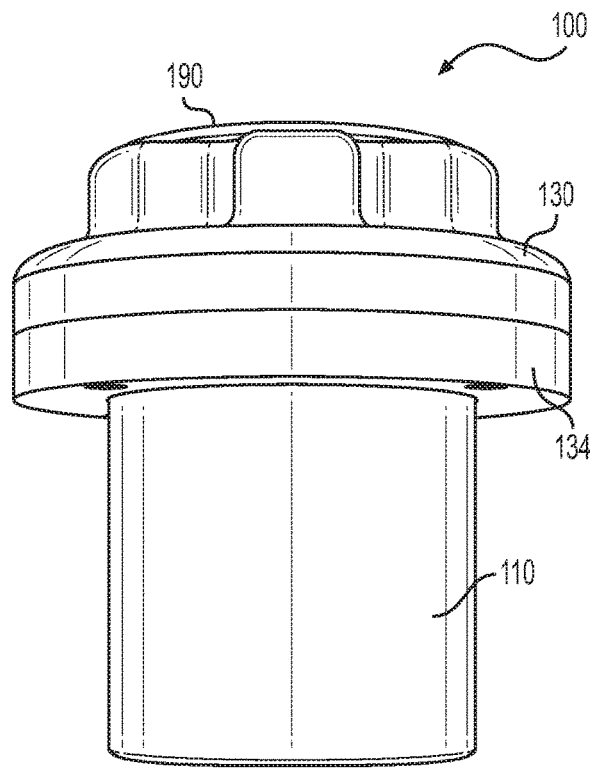
FIG. 6 is a front perspective view of the storage container of FIG. 5.
Figure 7:
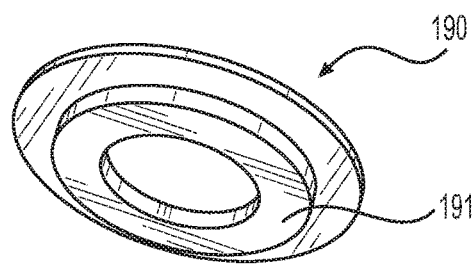
FIG. 7 is a bottom perspective view of the lid of FIG. 5.
Figure 10:
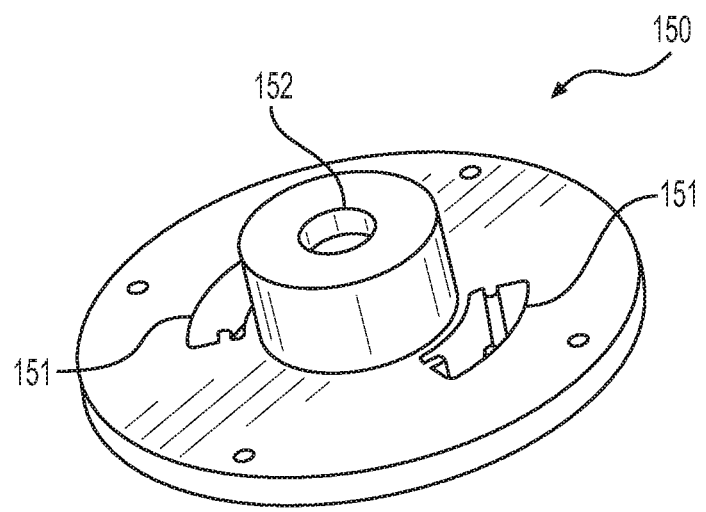
FIG. 10 is a top perspective view of an example valve cover.

The storage container 100 includes a removable lid 190 to prevent contamination of the heart valve 105 and other storage container 100 components. FIGS. 5, 6 and 8 illustrate the storage container 100 of FIG. 1 with the lid 190 coupled to the top cover 130. The lid 190 is sized and configured to be removably press fit (interference fit) into the threaded opening 132 of the top cover 130. FIG. 7 provides a bottom perspective view of the lid 190 illustrating a raised annular surface 191 projecting from the bottom of the lid 190 for engaging the threaded opening 132 of the top cover 130 of the storage container 100. It is also contemplated that the lid 190 can couple to the top cover 130 using a snap fit, a threaded connection, or using any other reversible fastener known in the art. The storage container 100 can be used for storing bioprosthetic heart valves having leaflets that require wet storage in a liquid sterilant/preservative. Therefore, when the lid 190 is coupled to the top cover 130, the storage container 100 is desirably leak-proof. The various components of the storage container 100 can be made of a variety of corrosion resistant materials, preferably molded polymers.

As will be described in more detail below, a crimping mechanism 120 is incorporated into the container 100. The crimping mechanism 120 engages the heart valve 105 and is operable to convert the heart valve 105 from a larger diameter in its expanded configuration to a smaller diameter in its crimped configuration upon opening the container and removal of the valve from the container 100. FIGS. 9A and 9B provide cross-section views of the storage container 100 of FIG. 1 taken along the section lines illustrated in FIG. 3. FIGS. 9A and 9B illustrate the various components of the crimping mechanism 120 including the top cover 130, a base 140, a valve cover 150, a valve stage 160, and a valve support 170.

Figure 13:
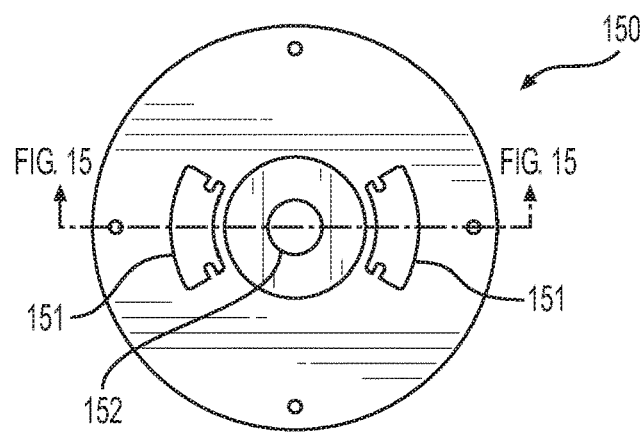
FIG. 13 is at top view of the valve cover of FIG. 10.
Figure 14:
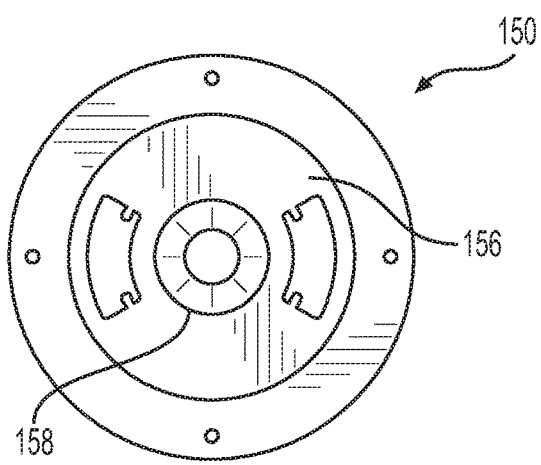
FIG. 14 is a bottom view of the valve cover of FIG. 10.
Figure 15:
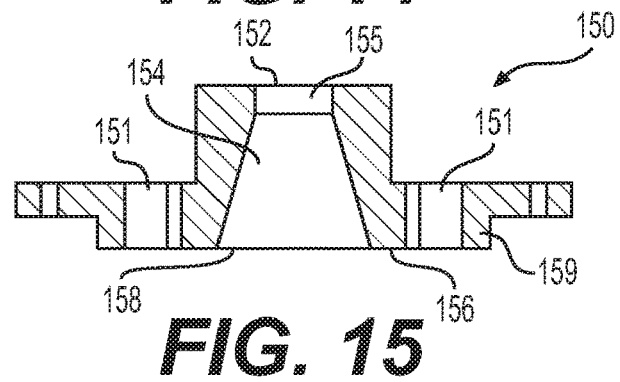
FIG. 15 is a section view of the valve cover of FIG. 13.

FIGS. 10-14 provide various view of an example valve cover 150. FIG. 15 provides a cross-section of the valve cover 150 taken along the section lines illustrated in FIG. 13. The valve cover 150 includes a central opening 152 in communication with the interior of the container housing 110. As will be described in more detail below, as the heart valve 105 is pushed through valve cover 150 and out the central opening 152, it is converted from its larger expanded configuration to its smaller unexpanded/crimped configuration. The diameter of the central opening 152 corresponds to the diameter of the heart valve 105 in the crimped configuration. As illustrated in FIG. 15, the valve cover 150 includes a tapered channel 154 extending from a bottom opening 158 on the bottom surface 156 of the valve cover 150 to the central opening 152. The tapered channel 154 can define a cone-shaped passage. The tapered channel 154 can also include a cylindrically-shaped portion 155 adjacent the central opening 152. This cylindrically-shaped portion 155 can help maintain the heart valve 105 in its crimped configuration and in a secure position for attachment to a delivery device. The dimension/diameter of the opening 158 provided on the bottom surface 156 of the valve cover 150 is sized and configured to correspond to the dimension/diameter of the heart valve 105 in the expanded configuration. The opening 158 can also have a dimension/diameter larger than the dimension/diameter of the heart valve 105 in the expanded configuration.

Figure 11:
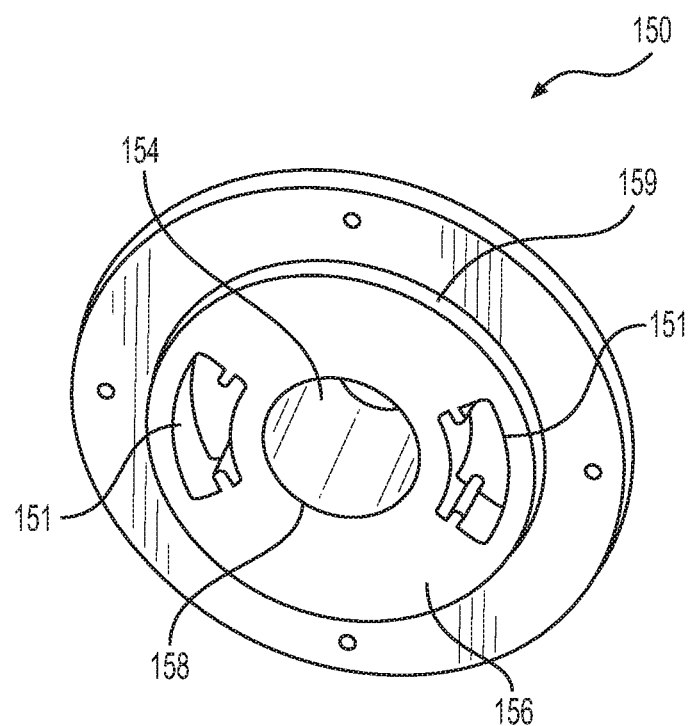
FIG. 11 is a bottom perspective view of the valve cover of FIG. 10.
Figure 12:
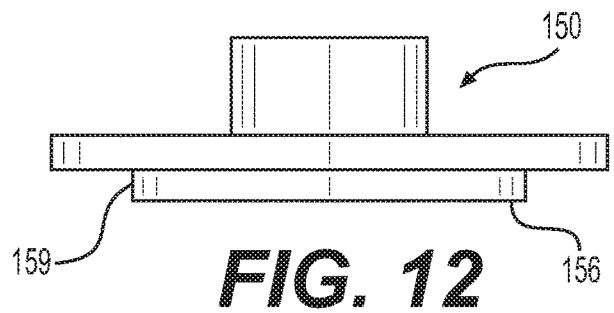
FIG. 12 is a front view of the valve cover of FIG. 10.

As illustrated in FIGS. 11, 12 and 15, the bottom surface 156 of the valve cover 150 includes a cylindrically-shaped projection 159. As provided in FIGS. 9A and 9B, this projection 159 is sized to extend into, and help position, the valve cover 150 with respect to the container housing 110.

The valve cover 150 can be fixedly connected to the container housing 110 such that the valve cover 150 cannot move axially and/or rotationally with respect to the container housing 110. For example, the valve cover 150 can be coupled to the container housing 110 by a number of screws positioned around the circumference of the valve cover 150. It is contemplated that the valve cover 150 could be coupled to the container housing 110 using any suitable known fastener. As will be described in more detail below, with the valve cover 150 fixed to the container housing 110, rotation of the top cover 130 allows the heart valve 105 (supported by base 140) to move axially within the storage container 100 and ultimately out through opening 152. As such, the heart valve 105 is converted from its larger expanded configuration to its smaller crimped configuration upon removal from the container.

FIGS. 16-20 provide various views of an example base 140. The base 140 includes a central cavity 143 sized to receive the heart valve 105, as illustrated in FIGS. 9A and 9B. The base 140 is axially movable with respect to the valve cover 150 and the top cover 130 for moving the heart valve 105 through the central opening 152 of the valve cover 150.

The base 140 includes an engagement feature for mating with the top cover 130 to facilitate axial movement of the base 140. For example, as illustrated in FIG. 9B, the top cover 130 includes a threaded opening 132 axially aligned with the opening 152 of the valve cover 150. The base 140 can include an exterior thread 142 for rotatably coupling with the threaded opening 132 of the top cover 130.

As illustrated in FIG. 9B, a portion of the base 140 extends through the valve cover 150 to threadingly engage the threaded opening 132 of the top cover 130. For example, as provided in FIG. 16, the exterior thread 142 is provided on one or more arms 144 of the base 140. The arms 144 extend up from a generally horizontal end surface 145 of the base 140. In assembly, the arms 144 extend through openings 151 provided in the valve cover 150 (shown in FIG. 13) to engage the threaded opening 132 of the top cover 130. In an example storage container 100, the arms 144 are sized and configured to move freely through the openings 151 in the valve cover 150 and do not engage or contact the valve cover 150 during axial movement of the base 140. FIGS. 13 and 14 of the valve cover 150 illustrate example arcuate shaped openings 151 for accommodating through movement of the arms 144 of the base 140.

Figure 21:
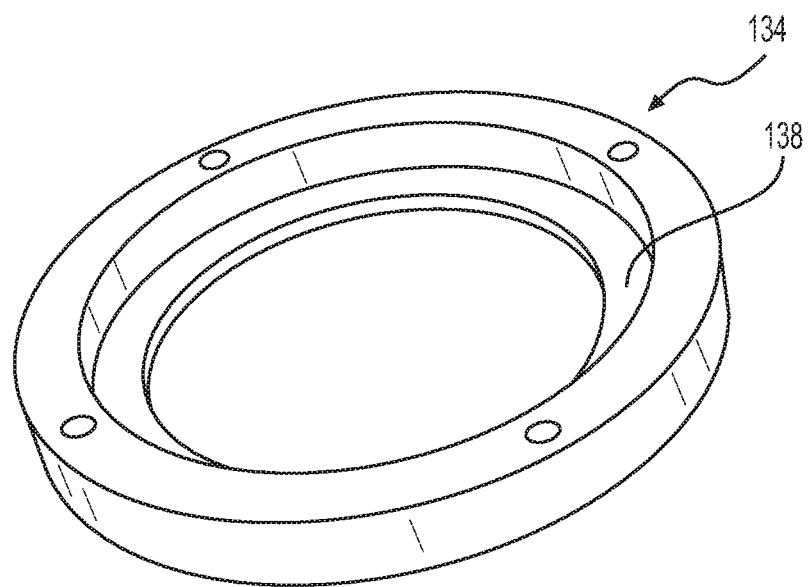
FIG. 21 is a perspective view of an example lower flange.
Figure 22:
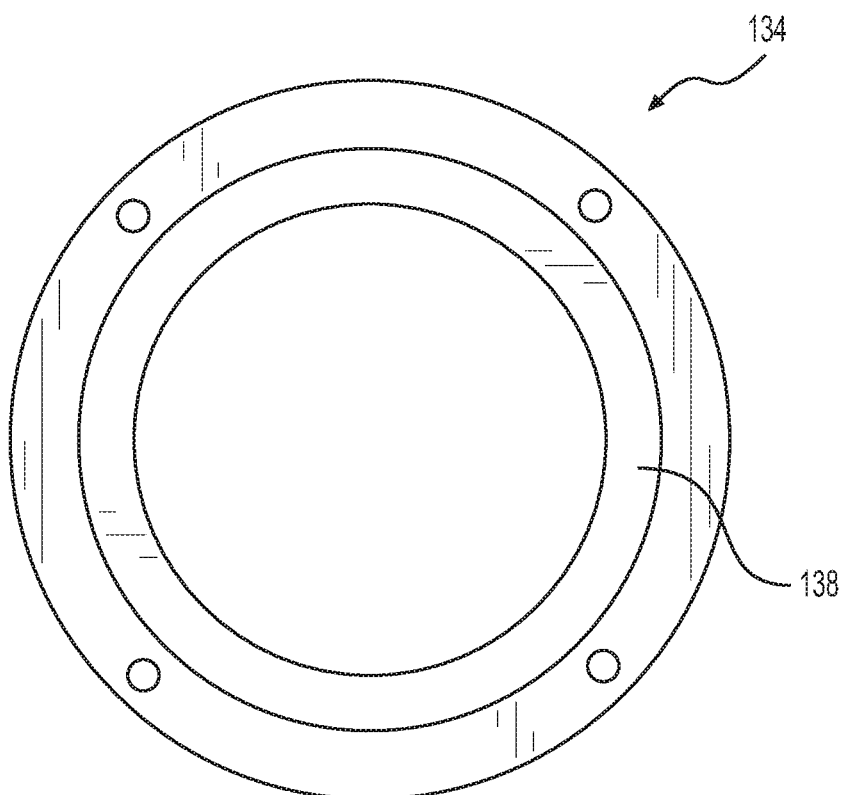
FIG. 22 is a bottom view of the lower flange of FIG. 21.

The storage container 100 includes a lower flange 134 for axially fixing the container housing 110, valve cover 150, and top cover 130. FIGS. 21 and 22 provide perspective and top views, respectively, of the lower flange 134. As provided in FIGS. 9A and 9B, the lower flange 134 is coupled to a bottom surface 136 of the top cover 130 such that the lower flange 134 is fixedly connected, axially and rotationally, with respect to the top cover 130. The lower flange 134 can be coupled to the top cover 130 by a number of screws positioned around the circumference of the lower flange 134. It is contemplated that the lower flange 143 can be coupled to the top cover 130 using any suitable fastener known in the art. A recessed shoulder 138 provided on the lower flange 134 can be sized to provide a gap or space 139 between the lower flange 134 and the container housing 110 and the valve cover 150. The inclusion of this gap/spacing 139 allows the top cover 130 and lower flange 143 to rotate independently of the container housing 110 and valve cover 150 (the container housing 110 being fixedly connected to the valve cover 150).

Figure 24:
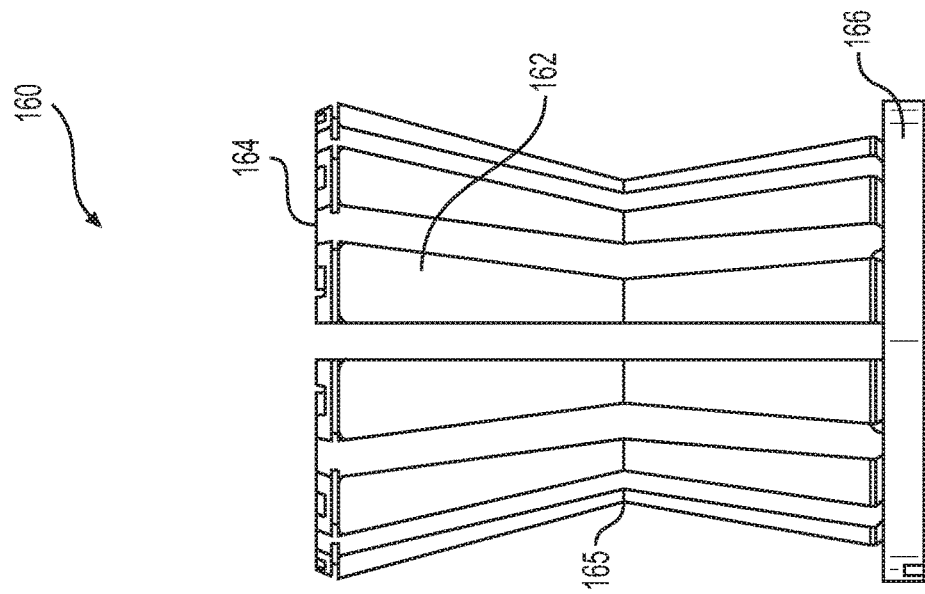
FIG. 24 is a front view of the valve stage of FIG. 23.
Figure 23:
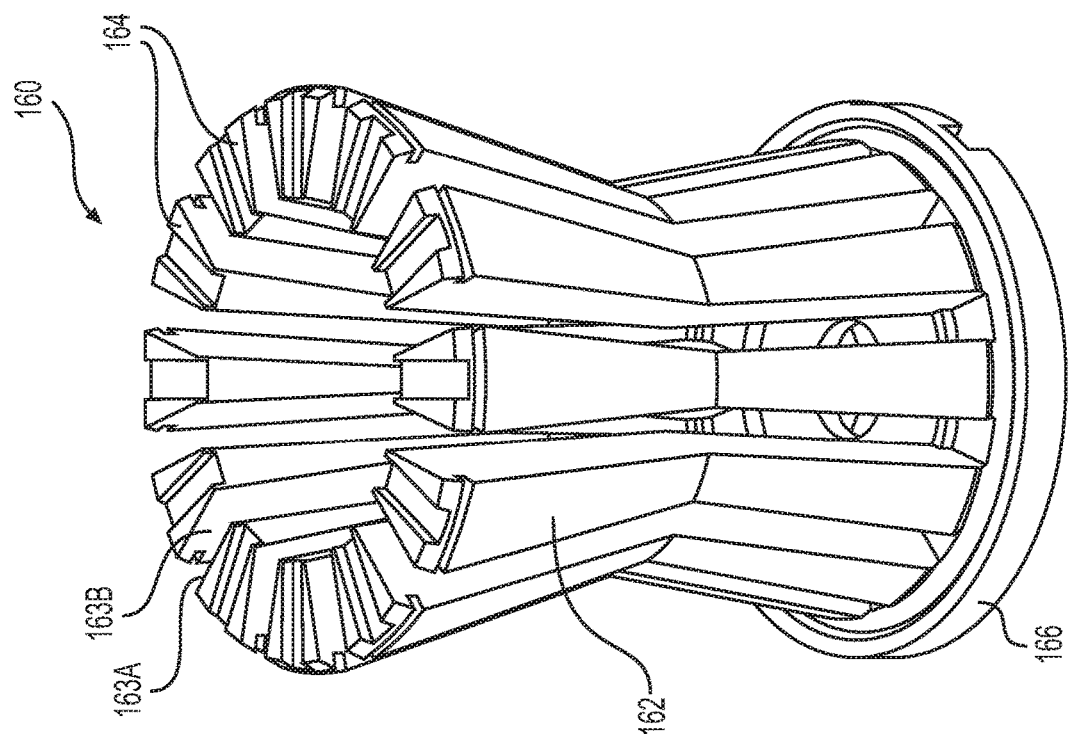
FIG. 23 is a perspective view of an example valve stage.
Figure 25:
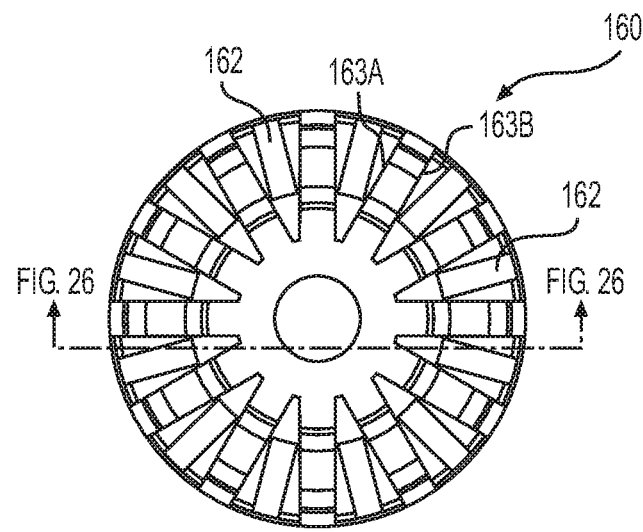
FIG. 25 is a top view of the valve stage of FIG. 23.
Figure 26:
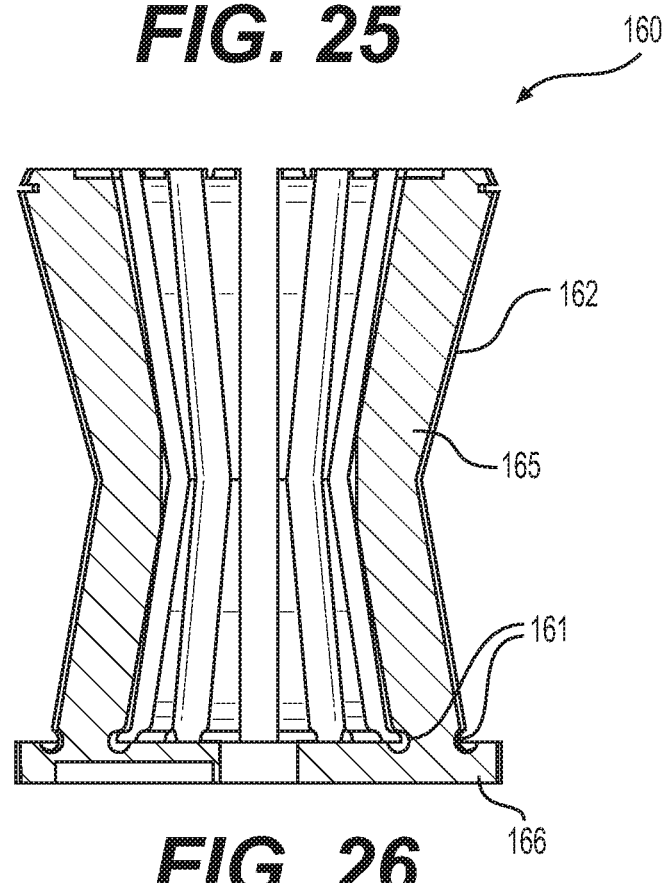
FIG. 26 is a section view of the valve stage of FIG. 25.

FIGS. 23-25 provide various views of an example valve stage 160. FIG. 26 is a cross-section view of the valve stage 160 taken along the section line illustrated in FIG. 25. The valve stage 160 is located within the central cavity 143 of the base 140. The heart valve 105 is positioned on the valve stage 160 such that the valve stage 160 provides axial support for the heart valve 105. The valve stage 160 can include multiple arms 162 extending up from a base structure 166 of the valve stage 160. As illustrated in FIGS. 23 and 25, the arms 162 can be equally spaced around the circumference of the valve stage 160. The top surface 164 of the arms 162 provides the support surface for the heart valve 105. The arms 162 can move radially. That is, the ends of the arms 162 can move radially in towards the longitudinal axis of the valve stage 160, resulting in a radial compression of the valve stage 160 proximate the end of the arms 162. The arms 162 are fixed to the base structure 166, but flexure features (such as cutouts 161 illustrated in FIG. 26) can be provided at the juncture between the arms 162 and the base structure 166. The arms 162 can also be constructed from a flexible material, to allow them to flex under compressive force (i.e., the force applied by the tapered channel 154 as the valve stage 160 is moved axially along with the base 140). This allows the arms 162 and the distal end of the valve stage 160 to contract slightly as it is pushed into the tapered channel 154 during crimping of the heart valve 105. It is also contemplated that the valve stage 160 can be used to limit axial movement of the base 140 and help push the heart valve 105 through the tapered channel 154. For example, as contact between the valve arms 162 and the tapered channel 154 causes the arms 162 to move radially inward, the arms 162 will reach a point of ultimate compression thereby preventing any further axial movement of the valve stage 160 and the base 140. As illustrated in FIGS. 23 and 25, the arms 162 can define a wedge-shape in cross-section. This wedge-shape allows the arms 162 to compress until the adjacent side walls 163A and 163B of the wedge-shape arms 162 contact. The arms 162 can also include a bend 165 along the length of the arm 162. This bend 165 provides for further compression/radial movement of the arms 162.

Figure 27:
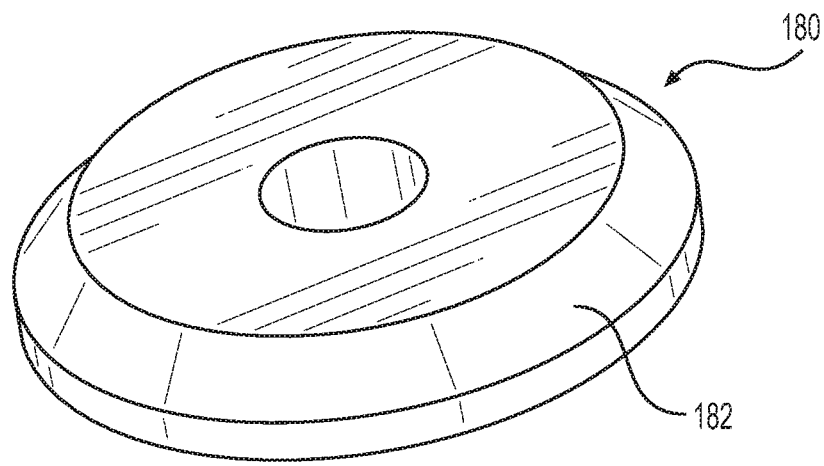
FIG. 27 is a perspective view of an example support ring.
Figure 28:
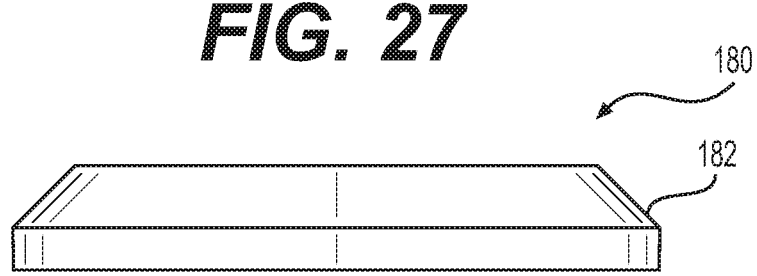
FIG. 28 is a front view of the support ring of FIG. 27.
Figure 29:
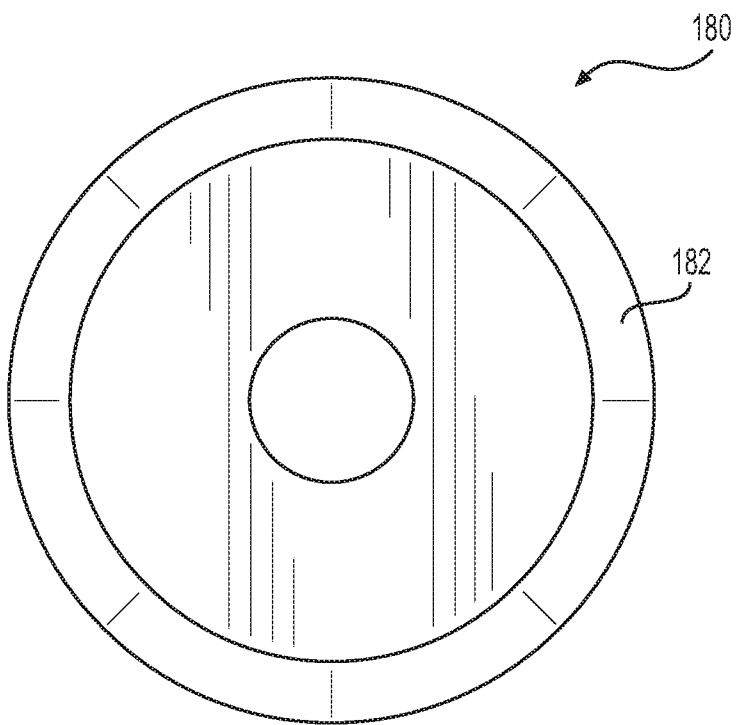
FIG. 29 is a top view of the support ring of FIG. 27.

FIGS. 27-29 provide various views of an example support ring 180. The crimping mechanism 120 can include a support ring 180 positioned at the top surface 164 of the valve stage 160 as illustrated in FIGS. 9A and 9B. The support ring 180 helps position the heart valve 105 on the valve stage 160 and within the tapered channel 154. As illustrated in FIGS. 27 and 28, the support ring 180 includes a tapered edge 182 that provides a contact point for the heart valve 105 and centers the heart valve 105 on the support ring 180.

FIGS. 30-33 provide various views of an example valve support 170. The crimping mechanism 120 includes a valve support 170 that extends axially adjacent to the heart valve 105 as illustrated in FIG. 9A. During axial movement of the base 140 and/or crimping of the heart valve 105, the valve support 170 can provide radial and/or lateral support for the heart valve 105. The valve support 170 can include axially extending arms 172 that extend from a base structure 174. The arms 172 can define a curved inner surface 176 corresponding in size and shape to the outer surface of the heart valve 105.

Figure 18:
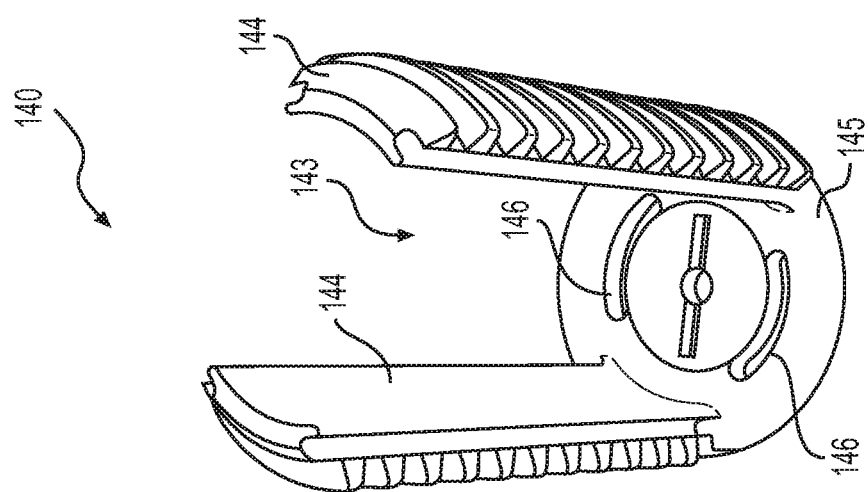
FIG. 18 is a perspective view of the base of FIG. 16.
Figure 17:
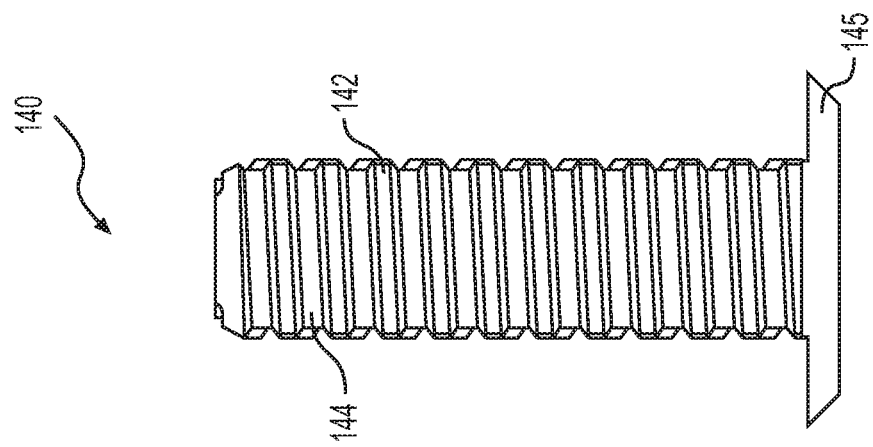
FIG. 17 is a side view of the base of FIG. 16.
Figure 16:
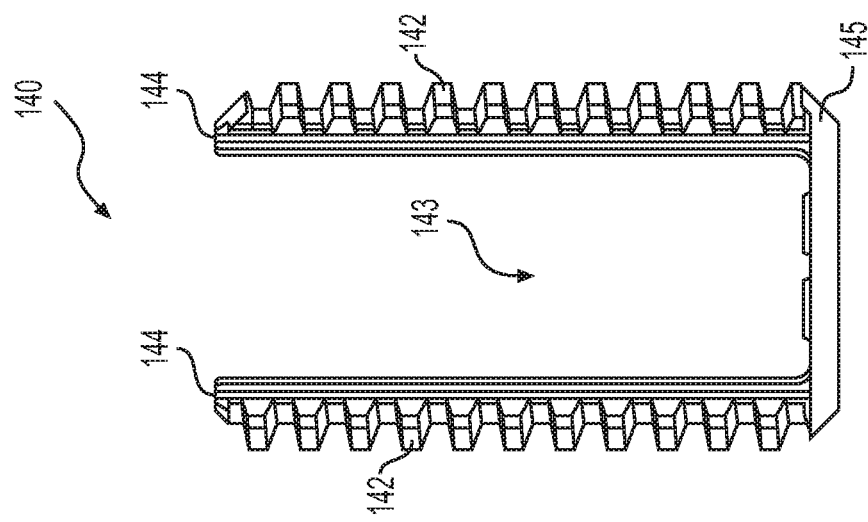
FIG. 16 is a front view of an example base.
Figure 19:
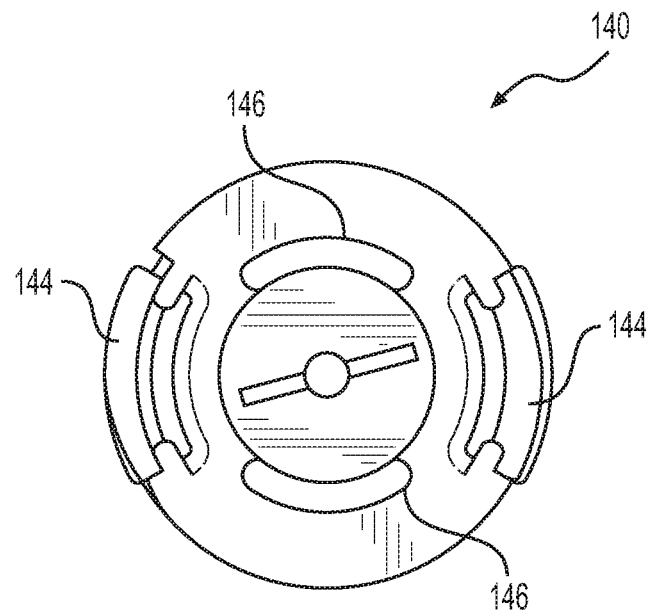
FIG. 19 is a top view of the base of FIG. 16.
Figure 20:
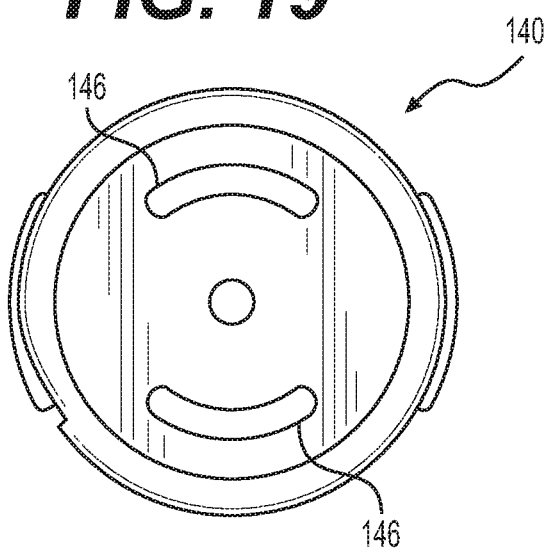
FIG. 20 is a bottom view of the base of FIG. 16.

The valve support 170 remains fixed axially within the container housing 110 during crimping of the heart valve 105. That is, as the base 140 moves axially towards/away from the top cover 130, the arms 172 of the valve support 170 extend/pass through openings 146 provided in the base 140. In an example storage container 100, the arms 172 are sized and configured to move freely through the openings 146 in the base 140. FIGS. 18-20 illustrate arcuate-shaped openings 146 for accommodating through movement of the arms 172. As illustrated in FIG. 9A, the base structure 174 is positioned under the base 140, and between the base 140 and the container housing 110.

Figure 31:
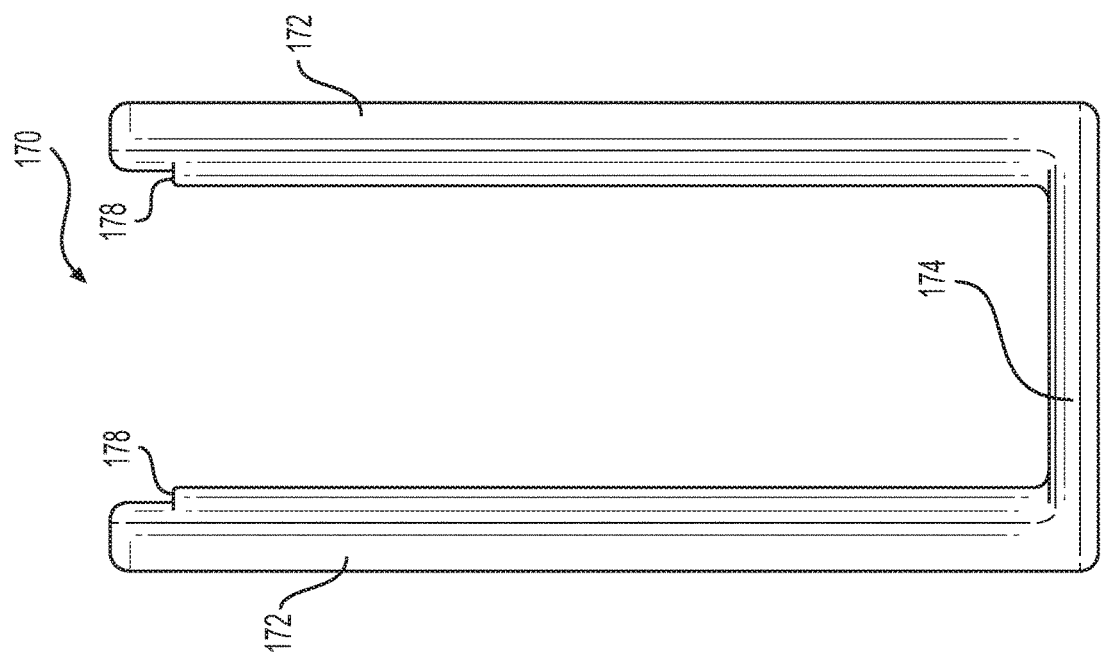
FIG. 31 is a front view of the valve support of FIG. 30.
Figure 30:
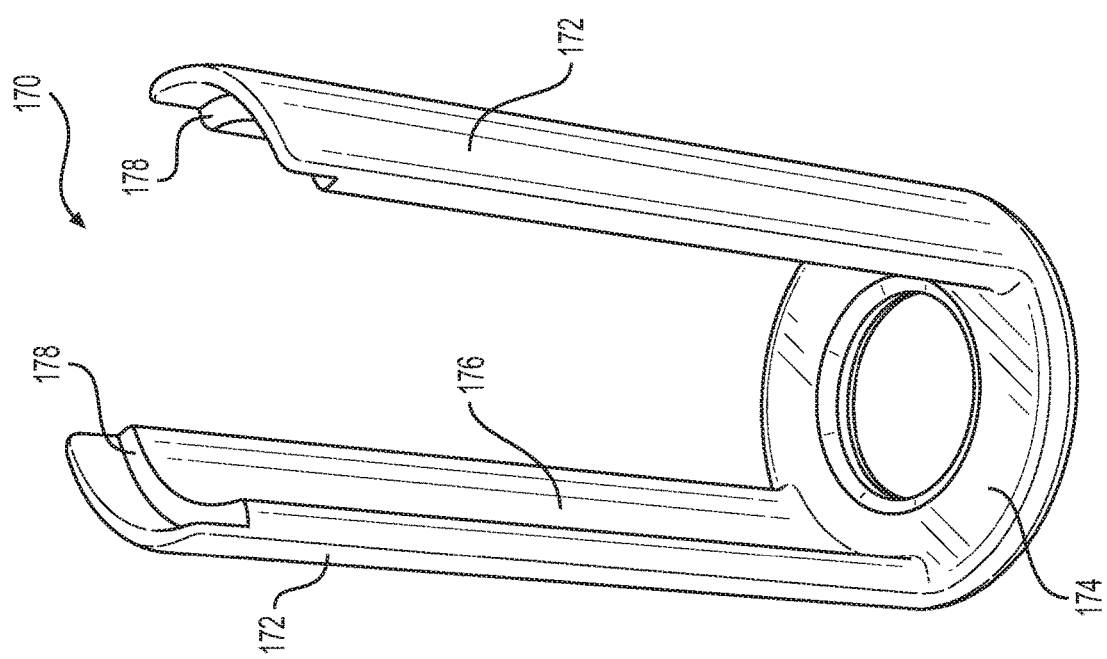
FIG. 30 is a perspective view of an example valve support.
Figure 33:
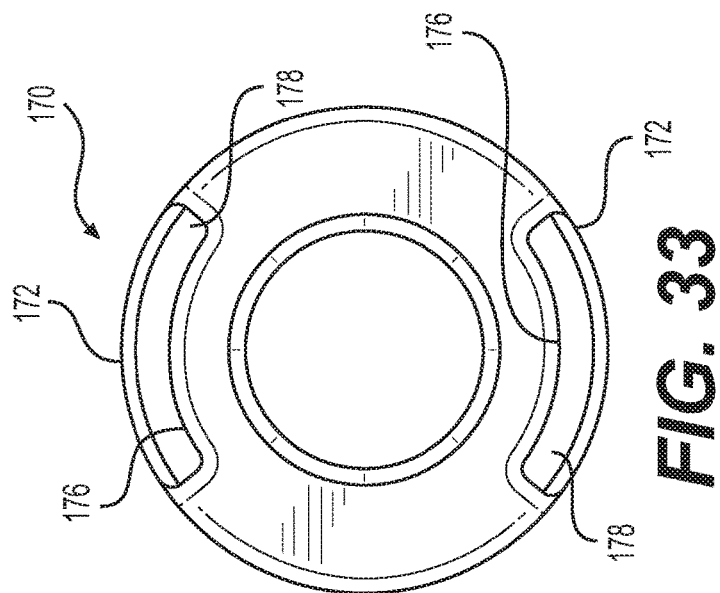
FIG. 33 is a top view of the valve support of FIG. 30.
Figure 32:
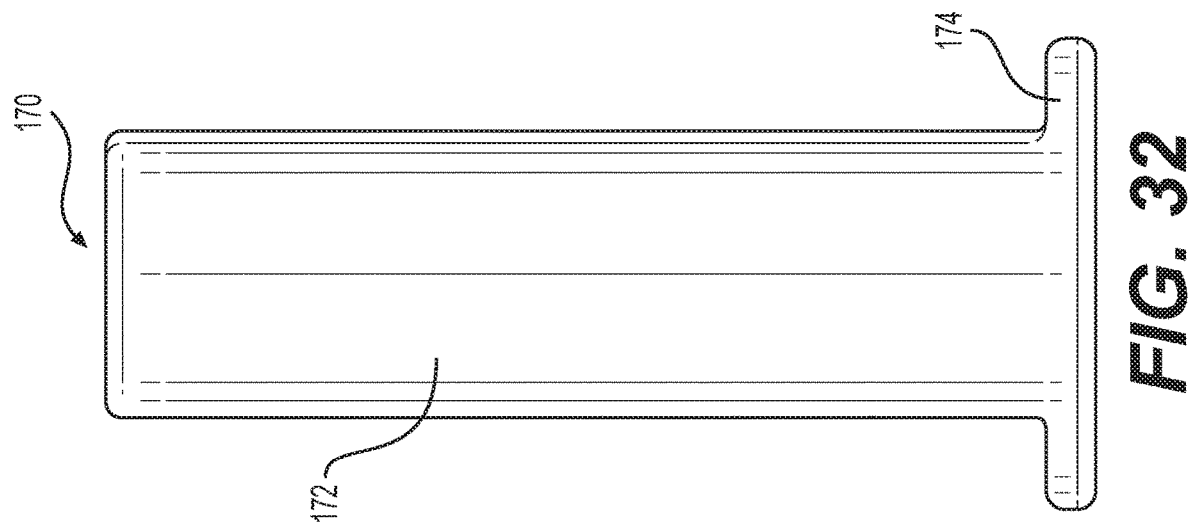
FIG. 32 is a side view of the valve support of FIG. 30.
Figure 34:
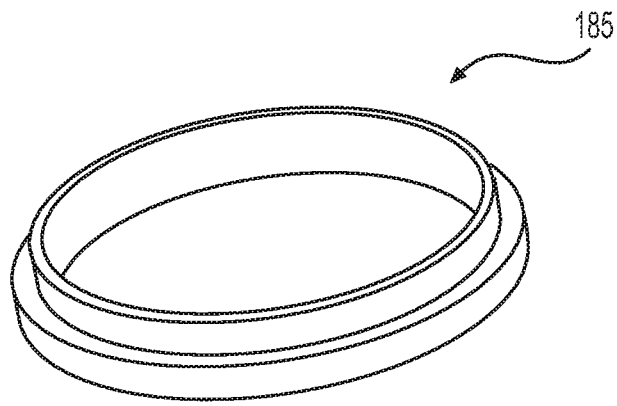
FIG. 34 is a perspective view of an example valve support ring.
Figure 35:
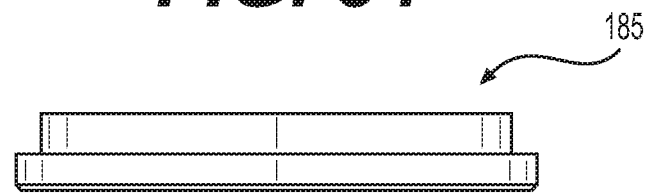
FIG. 35 is a front view of the valve support ring of FIG. 34.
Figure 36:
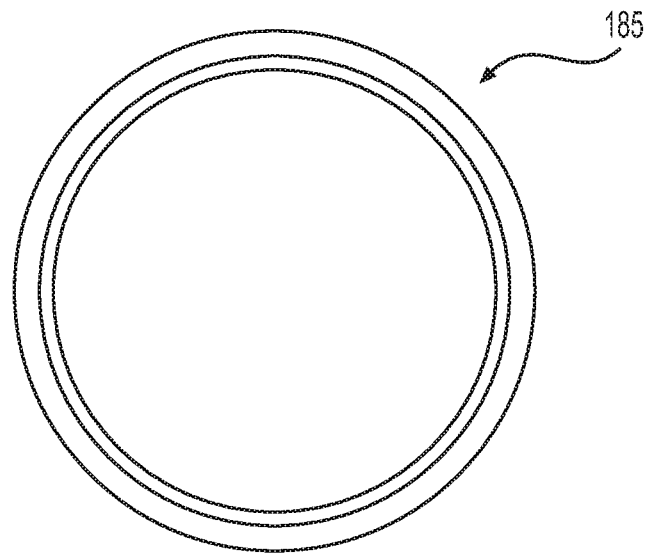
FIG. 36 is a top view of the valve support ring of FIG. 34.

FIGS. 34-36 provide various views of an example upper valve support ring 185. The crimping mechanism 120 includes an upper valve support ring 185 positioned at the lower surface 156 of the valve cover 150 proximate the opening 158 to the tapered channel 154 as illustrated in FIGS. 9A and 9B. As shown in FIGS. 30 and 31, the distal end of the arms 172 of the valve support 170 can include a recessed surface 178 for accommodating the upper valve support ring 185. The upper valve support ring 185 can be positioned above the heart valve 105 and can be used to secure the heart valve 105 in the container 110 in its expanded configuration. The upper support ring 185 can also be used to guide the heart valve 105 into the tapered channel 154 and ease the transition (from the expanded configuration) into the valve cover 150 and towards the crimped configuration.

As mentioned above, a preferred heart valve 105 includes a stent body and a plurality of flexible leaflets. If the leaflets need to remain hydrated during storage, such as if they are made of bioprosthetic material, the entire container housing 110 is filled with a liquid sterilant/preservative solution. To facilitate preparation of the heart valve 105 prior to implantation, the container housing 110 and/or top cover 130 can include a drain hole (not shown). Alternatively, the lid 190 can be removed from the top cover 130 and unwanted fluid can be drained by tilting or inverting the storage container 100.

Prior to implantation of the heart valve 105, the preservative solution (if present) can be drained from within the container housing 110. If desired, the lid 190 can be removed and the heart valve 105 rinsed while the heart valve 105 remains within the container housing 110, thereby reducing the chance of damage to the valve 105. The heart valve 105 can then be crimped by passing the heart valve 105 through the crimping mechanism 120. The user can grasp the container housing 110 to hold it in a fixed position whiling rotating the top cover 130. Rotation of the top cover 130 allows the exterior thread 142 on the arms 144 of the base 140 to engage the threaded opening 132 in the top cover 130, resulting in axial movement of the base 140. Axial movement of the base 140 results in a corresponding axial movement of the heart valve 105 toward and through the tapered channel 154 of the valve cover 150. As the heart valve 105 is moved through the tapered channel 154, and ultimately out through opening 152, radial pressure provided by the tapered channel 154 compresses the heart valve 105 and the heart valve 105 is converted from its larger expanded configuration to its smaller crimped configuration. If desired, a constraint can be provided around the heart valve 105 to maintain it in the crimped configuration and/or further crimp the heart valve 105. The heart valve 105 can then be detached from the storage container 100 and mounted to a delivery device for implantation.

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above, but should be determined only by a fair reading of the claims that follow.

What is claimed is:

1. A storage container for a prosthetic heart valve, comprising:
    a container housing sized to receive a heart valve in an expanded configuration; and
    a crimping mechanism incorporated into the storage container and operable to engage a heart valve and convert a heart valve from its expanded configuration to its crimped configuration as it exits the container housing, the crimping mechanism including:
    a valve cover coupled to the container housing, the valve cover including a central opening in communication with an interior of the container housing for allowing passage of a heart valve therethrough, and
    a base received within the container housing, the base having a central cavity sized and configured to receive a heart valve, the base axially movable with respect to the valve cover and the container housing for moving a heart valve through the central opening of the valve cover,
    wherein axial movement of the base towards the valve cover causes a portion of the base to extend through an opening provided in the valve cover.

2. The storage container of claim 1,
    wherein movement of a heart valve through the central opening converts a heart valve from its expanded configuration to its crimped configuration.

3. The storage container of claim 2, wherein the valve cover includes a tapered channel extending from a bottom surface to the central opening, and
    wherein movement of a heart valve through the tapered channel converts a heart valve from its expanded configuration to its crimped configuration.

4. The storage container of claim 3, wherein the tapered channel defines a cone-shaped passage.

5. The storage container of claim 3, wherein a size of an opening to the tapered channel at the bottom surface corresponds to the size of a heart valve in its expanded configuration.

6. The storage container of claim 1, wherein the crimping mechanism further includes:
    a top cover coupled to the container housing such that the valve cover is located between the top cover and the container housing, the top cover including an opening axially aligned with the central opening of the valve cover for allowing passage of a heart valve therethrough.

7. The storage container of claim 6, wherein the valve cover is fixed to the container housing.

8. The storage container of claim 6, wherein an outer surface of the container housing includes a radially projecting shoulder that is received within a corresponding recess provided in the top cover such that the top cover is rotatably coupled to the container housing and the valve cover.

9. The storage container of claim 6, wherein the opening of the top cover is a threaded opening,
    wherein the base includes an arm comprising the portion of the base that extends through the opening in the valve cover, the arm including an exterior thread for engaging the threaded opening of the top cover, and
    wherein rotation of the top cover causes the threaded opening to engage the exterior thread of the base and move the base axially with respect to the top cover and move the arm axially through the opening in the valve cover.

10. The storage container of claim 6, wherein the crimping mechanism further includes a valve stage located within a central cavity of the base, the valve stage configured to provide axial support for a heart valve.

11. The storage container of claim 6, wherein the crimping mechanism further includes a valve support configured to extend axially adjacent a heart valve and to provide radial or lateral support for a heart valve, the valve support including an axially extending arm extending from a base structure,
    wherein the arm passes through an arm opening provided in the base such that the valve support is fixed axially within the container housing during movement of the base with respect to the valve cover.

12. A system for storing and crimping an expandable prosthetic heart valve, comprising:
    an expandable prosthetic heart valve having both crimped and expanded configurations, the heart valve comprising an annular frame with a leaflet structure positioned within frame,
    a container housing sized to receive the heart valve in its expanded configuration;
    a crimping mechanism incorporated into the container housing and engaging the heart valve that is operable to convert the heart valve from its expanded configuration to its crimped configuration as it exits the container housing, the crimping mechanism including:
    a valve cover coupled to the container housing, the valve cover including a central opening in communication with an interior of the container housing for allowing passage of the heart valve therethrough, and
    a base received within the container housing, the heart valve the base having positioned within a central cavity of the base, the base axially movable with respect to the valve cover and the container housing for moving the heart valve through the central opening of the valve cover, wherein axial movement of the base towards the valve cover causes a portion of the base to extend through an opening provided in the valve cover.

13. The system of claim 12, wherein the container housing holds a solution suitable for preserving the leaflet structure.

14. The system of claim 12, wherein the crimping mechanism includes:
wherein movement of the heart valve through the central opening converts the heart valve from its expanded configuration to its crimped configuration,
wherein a central longitudinal axis of the base is co-axial with a central longitudinal axis of the central opening of the valve cover.

15. The system of claim 12, wherein the crimping mechanism includes:
a top cover rotatably coupled to the valve cover and the container housing, the top cover having an opening axially aligned with the central opening of the valve cover.

16. The system of claim 15, wherein the opening of the top cover is a threaded opening,
wherein the base includes an exterior thread for engaging the threaded opening of the top cover, the base being rotatably coupled to the top cover, and
wherein rotation of the top cover causes the threaded opening to engage the exterior thread of the base and move the base axially with respect to the top cover.

17. The system of claim 12, wherein the valve cover includes a tapered channel extending from a bottom surface of the valve cover to the central opening of the valve cover, and
wherein movement of the heart valve through the tapered channel converts the heart valve from its expanded configuration to its crimped configuration.

18. A method of storing and crimping an expandable prosthetic heart valve, the method comprising:
providing a prosthetic heart valve having a crimped configuration sized to be delivered to a site of implantation through a catheter and an expanded configuration sized to engage a heart valve annulus;
storing the heart valve in a container in its expanded configuration, the container including:
a container housing,
a valve cover coupled to the container housing and including a central opening in communication with an interior of the container housing,
a base received within the container housing, the base rotatably coupled to the valve cover and axially movable with respect to the valve cover and container housing, the heart valve received within a central cavity of the base; and
converting the heart valve from its expanded configuration to its crimped configuration as it passes through the central opening of the valve cover.

19. The method of claim 18,
wherein the step of converting further comprises compressing the heart valve through a tapered channel provided in the container.

20. The method of claim 18, wherein the container includes:
wherein the step of converting further comprises axially moving the base with respect to the valve cover to advance the heart valve from the central cavity of the base through the central opening of the valve cover.

21. The method of claim 20, wherein the container includes:
a top cover rotatably coupled to the valve cover and the container housing, the top cover having a threaded opening axially aligned with the central opening of the valve cover,
the base including an exterior thread for engaging the threaded opening of the top cover,
wherein the step of converting further comprises rotating the top cover to cause the threaded opening to engage the exterior thread of the base, thereby moving the base axially with respect to the top cover.

22. The method of claim 20, further maintaining the valve in its crimped state using a constraint around the valve, and detaching the valve from the container after placing the constraint around the valve and mounting the valve on a delivery catheter.

* * * * *